United States Patent [19]

Fenderson et al.

[11] Patent Number: 5,900,389
[45] Date of Patent: May 4, 1999

[54] SYNERGISTIC HERBICIDAL COMPOSITIONS OF DIMETHENAMID AND UREA HERBICIDIES

[76] Inventors: John M. Fenderson, 902 Hardtner St., Box 47, Kiowa, Kans. 67070; William B. O'Neal, 432 Town Place Cir., Buffalo Grove, Ill. 60089; Théo Quaghebeur, Rue des Résistants 54, B-7030 Saint-Symphorien, Belgium; Karl-Christoph Schumm, Rua Paraguacu, 74, 13.044-230 Campinas—5P, Brazil; Walter Van Loocke, Heerweg 10, B-8377 Meetkerke, Belgium

[21] Appl. No.: 08/914,349

[22] Filed: Aug. 15, 1997

Related U.S. Application Data

[60] Division of application No. 08/467,367, Jun. 6, 1995, Pat. No. 5,721,191, which is a continuation-in-part of application No. 08/153,946, Nov. 16, 1993, abandoned, which is a continuation of application No. 08/019,386, Feb. 18, 1993, abandoned, and a continuation-in-part of application No. 08/152,066, Nov. 12, 1993, abandoned, which is a continuation-in-part of application No. 08/019,933, Feb. 19, 1993, abandoned, and a continuation of application No. 08/236,732, May 2, 1994.

[30]     Foreign Application Priority Data

Jun. 25, 1993 [GB] United Kingdom ................... 9313210

[51] Int. Cl.⁶ .......................... A01N 43/10; A01N 43/40; A01N 47/36; A01N 47/30
[52] U.S. Cl. ........................... 504/129; 504/130; 504/131
[58] Field of Search ..................................... 504/129, 130, 504/139

[56]           References Cited

U.S. PATENT DOCUMENTS

| | | | |
|---|---|---|---|
| 3,013,054 | 12/1961 | Richter | 260/473 |
| 4,666,502 | 5/1987 | Seckinger et al. | 70/91 |
| 4,695,673 | 9/1987 | Heather et al. | 568/310 |
| 4,789,393 | 12/1988 | Hanagan | 71/92 |

FOREIGN PATENT DOCUMENTS

| | | |
|---|---|---|
| 230 596 | 8/1987 | European Pat. Off. . |
| 315889 | 5/1989 | European Pat. Off. . |
| 338992 | 10/1989 | European Pat. Off. . |
| 380 447 | 1/1990 | European Pat. Off. . |
| 394889 | 10/1990 | European Pat. Off. . |
| 461079 | 12/1991 | European Pat. Off. . |
| 549524 | 6/1993 | European Pat. Off. . |
| WO 91/10653 | 7/1991 | WIPO . |

OTHER PUBLICATIONS

The Agrochemicals Handbook: Diuron, Forchlorfenuron, Linuron, Tebuthiuron, Thiadiazuron, Aug. 1991.

*Weed Control And Soil Persistence Studies With Dimethenamid In Maize*, A. Rahman and T.K. James; Proc. 45th N.Z. Plant Protection Conf. 1992: 84–88.

*Herbicidal Composition*, Kimura et al.; United States Statutory Invention Registration, Reg. No. H670, Sep. 5, 1989.

*SAN 582 H—A New Herbicide For Weed Control In Corn And Soybeans*, J. Harr, K. Seckinger, E. Ummel, Brighton Crop Protection Conference—Weeds, 1991, pp. 87–92.

*Weed Control in No–tillage and Conventional Corn (Zea may) with ICIA–0051 and SC–0774*, John S. Wilson and Chester L. Foy; Weed Technology, 1990, vol. 4:731–738.

*Primary Examiner*—S. Mark Clardy
*Attorney, Agent, or Firm*—Alston & Bird LLP

[57]             ABSTRACT

Co-application of dimethenamid with urea herbicides provides improved herbicidal activity.

20 Claims, No Drawings

SYNERGISTIC HERBICIDAL COMPOSITIONS OF DIMETHENAMID AND UREA HERBICIDIES

This application is a division of application Ser. No. 08/467,367, now U.S. Pat. No. 5,721,191, filed Jun. 6, 1995, which is a continuation-in-part of application Ser. No. 08/153,946, filed Nov. 16, 1993, abandoned, which is a continuation of application Ser. No. 08/019,386, abandoned, filed Feb. 18, 1993; a continuation-in-part of application Ser. No. 08/152,066, abandoned, filed Nov. 12, 1993, which is a continuation-in-part of application Ser. No. 08/019,933, abandoned, filed Feb. 19, 1993, abandoned; and a continuation of application Ser. No. 08/236,732, filed May 2, 1994.

The present invention concerns a method of controlling undesired plant growth employing co-application of dimethenamid and at least one other herbicide, herbicidal compositions comprising dimethenamid and at least one other herbicide and the use of such compositions in controlling undesired plant growth.

Dimethenamid (FRONTIER®) whose chemical name is 2-chloro-N-(2,4-dimethyl-3-thienyl)-N-(2-methoxy-1-methylethyl)-acetamide, processes for its production, herbicidal compositions containing it and its use as a herbicide are described in U.S. Pat. No. 4,666,502 the contents of which are incorporated herein by reference. Dimethenamid consists of 4 stereoisomers due to two chiral elements and can thus also exist in the form of the individual isomers as diastereomeric mixtures (1S, aRS (known as S-dimethenamid) and 1R aRS (known as R-dimethenamid)) and as a racemic mixture (1RS, aRS). References herein to dimethenamid refer to its various forms unless otherwise stated. Of the diastereomeric mixtures S-dimethenamid is preferred.

The term herbicides, as used herein, refers to compounds which combat or control undesired plant growth. This class of compounds may be divided into sub-classes according to the primary type or mode of action the herbicide has on the plant. For example according to G. F. Warren of Purdue University, Indiana, USA, herbicides can be classified as auxin transport inhibitors, growth regulator herbicides, photosynthesis inhibitors, pigment inhibitors, growth inhibitors, amino acid synthesis inhibitors, lipid biosynthesis inhibitors, cell wall biosynthesis inhibitors, rapid cell membrane disruptors as well as "miscellaneous" herbicides which do not come under one of the preceding categories.

It has now surprisingly been found that co-application of dimethenamid and at least one other herbicide results in better and in some cases longer-lasting control of undesired plant growth. This synergistic effect exhibits itself in a high degree of control at co-application rates which are significantly lower than the rate of each individual compound required to obtain the same degree of control. Furthermore. at any given co-application rate the degree of control is higher than the additive effect obtained for the individual components at the same rate. In some cases both speed of activity and level of control are enhanced and/or weeds can be controlled which are not controlled by either component at economical rates.

This synergistic effect allows for satisfactory control at reduced application rates for each component and even at levels which if applied for a particular component alone would give insufficient control. Additionally, longer residual control may be achieved. This provides for significant economic and environmental advantages in the use of dimethenamid and the herbicide(s) used in combination therewith.

Co-application can be achieved using tank mixes of preformulated individual active ingredients, simultaneous or sequential (preferably 1–2 days) application of such formulations or application of preformulated fixed pre-mix combinations of the individual active ingredients.

Examples of herbicides which may be used in combination with dimethenamid in accordance with the invention include 1. auxin transport inhibitors, e.a. naptalam
2. growth regulators, including 1) benzoic acids. e.u. dicamba: h) phenoxy acids i) acetic acid type, e.g. 2,4-D, MCPA, ii) propionic acid type, e.g. 2,4-DP, MCPP, iii) butyric acid type, e.g. 2,4-DB, MCPB; c) picolinic acids and related compounds, e.g. picloram, triclopyr, fluroxypyr, clopyralid
3. photosynthesis inhibitors, including a) s-triazines i) chloro substituted, e.g. atrazine, simazine, cyanazine, ii) methoxy substituted, e.g. prometon, iii) methylthio substituted, e.g. ametryn, prometryn; b) other triazines, e.g. hexazinone, metribuzin; c) substituted ureas, e.g. diuron, fluometuron, linuron, tebuthiuron, thidiazuron, forchlorfenuron; d) uracils, e.g. bromacil, terbacil; e) others, e.g. bentazon, desmedipham, phenmnedipham, propanil, pyrazon, pyridate
4. pigment inhibitors, including a) pyridazinones, e.g. norflurazon; b) isoxazolones, e.g. clomazone; c) others, e.g. amitrole, fluridone
5. growth inhibitors, including a) mitotic disruptors i) dinitroanilines, e.g. trifluralin, prodiamine, benefin, ethalfluralin, isopropalin, oryzalin, pendimethalin; ii) others, e.g. DCPA, dithiopyr, thiazopyr, pronamide; b) inhibitors of shoots of emerging seedlings i) thiocarbamates, e.g. EPTC, butylate, cycloate, molinate, pebulate, thiobencarb, triallate, vemolate; c) inhibitors of roots only of seedlings, e.g. bensulide, napropamide, siduron; d) inhibitors of roots and shoots of seedlings, including chloroacetamides e.g. alachlor, acetochlor, metolachlor, diethatyl, propachlor, butachlor, pretilachlor, metazachlor, dimethachlor, and others e.g. cinmethylin
6. amino acid synthesis inhibitors, including a) glyphosate, glufosinate; b) sulfonylureas, e.g. riimsulfuron, metsulfuron, nicosulfuron, triasulfuron, primisulfuron, bensulfuron, chlorimuron, chlorsulfuron, sulfometuron, thifensulfuron, tribenuron, ethametsulfuron, triflusulfuron, clopyrasulfuron, pyrazasulfuron, prosulfuron (CGA-152005), halosulfuron, metsulfuron-methyl, chlorimuron-ethyl; c) sulfonamides, e.g. flumetsulam (a.k.a. DE498); d) imidazolinones, e.g. imazaquin, imazamethabenz, imazapyr, imazethapyr, imazmethapyr
7. lipid biosynthesis inhibitors, including a) cyclohexanediones, e.g. sethoxydim, clethodim; b) aryloxyphenoxys, e.g. fluazifop-(P-butyl), diclofop-methyl, haloxyfop-methyl, quizalofop; c) others e.g. fenoxaprop-ethyl
8. cell wall biosynthesis inhibitors, e.g. dichlobenil, isoxaben
9. rapid cell membrane disruptors, including a) bipyridiliums, e.g. paraquat, diquat; b) diphenyl ethers, e.g. acifluorfen, fomesafen, lactofen, oxyfluorfen; c) glutamine synthetase inhibitors, e.g. giufosinate; d) others, e.g. oxadiazon
10. miscellaneous, including a) carbamates, e.g. asulam; b) nitriles, e.g. bromoxynil, ioxynil; c) hydantocidin and derivatives; d) various, e.g. paclobutrazol, ethofumesate, quinclorac (a.k.a. BAS514), difenzoquat. endothall, fosamine, DSMA, MSMA 11. Others a) triketones and diones of the type described in U.S. Pat. Nos. 4,695,673; 4,869,748; 4,921,526; 5,006,150; 5,089,046, 5,336,662; and 5,608,101; the contents of each of which are incorporated herein by reference; and in EP-A-338,992; EP-A-394,889; BP-A-506,9071 EP-A 137,963; EP-A-186,118; EP-A-186,119s; EP-A-186,120; EP-A-249,150; and EP-A-336,898. Examples of such triketones and diones are sulcotrione (MIKADO®) whose chemical designation is 2-(2-chloro-4-methanesulfonylbenzoyl)-1,3-cyclohexane dione: 2-(4-methylsulfonyloxy-2-nitrobenzoyl)-4,4,6,6-tetramethyl-1,3-cyclohexanedione; 3-(4-methylsulfonyloxy-2-nitrobenzoyl)-bicyclo[3,2,1]octane -2,4-dione3-(4-methylsulfonyl-2-nitrobenzoyl)-bicyclo[3,2,1]octane-2,4-dione; 4-(4-chloro-2-nitrobenzoyl)-2,6,6-trimethyl-2H-1,2-oxazine-3,5(4H,6H)dione; 4-(4-methylthio-2-nitrobenzoyl)-2,6,6-trimethyl-2H-1,2-oxazine-3,5(4H,6H)-dione; 3-(4-methylthio-2-nitrobenzoyl)-bicyclo-[3,2,1] octane-2,4-dione;4-(2-nitro-4-trifluoromethoxybenzoyl )-2,6,6-trimethyl-2H-1,2-oxazine-3,5(4H,6H)-dione. b) Compounds of the type described in. U.S. Pat. No. 5,506,192, contents of which are incorporated herein by reference; EP-A-461,079; EP-A-b549,524; EP-A-315,889; and PCT Appln. No. 91/10653; including for example 3-[(4,6-dimethoxy-2-pyrimidinyl)hydroxymethyl]-N-methyl-2-pyridine carboxamnide; 4,7-dichloro-3-(4,6-dimethoxy-2-pyrimidinyl)-3-hexanoyloxyphthalide; 3-[(4,6-dimethoxy-2-pyrinidinyl)carbonyl]-N,N-dimethyl-2-pyridine carboxamide; 3,6-dichloro-2-[(4,6-dimethoxy-2-pyrirnidinyl)carbonyl]benzoic acid; 6-chloro-2-[(4,6-dimethoxy-2-pyrirnidinyl)thio] benzoic acid (a.k.a. DPX-PE350 or pyrithiobac) and salts thereof.

The present invention therefore concerns a method of combatting or controlling undesired plant growth or otherwise regulating plant growth which comprises co-applying to a locus where such combatting or control is desired an herbicidally or plant growth regulatinig effective aggregate amount of dimethenamid and at least one other herbicide.

Application rates for co-application will of course vary depending upon climatic conditions, season, soil ecology, weeds to be combatted and the like, however, successful results can be obtained e.g. with rates of dimethenatnid of 0.1 to 3.0 kg/ha, preferably 0.1 to 2.0 kg/ha, especially 0.25 to 1.5 kg/ha e.g. 0.9 to 1.5 kg/ha in co-application with rates for partner herbicides which correspond to or are significantly lower than recommended for use thereof individually.

The suitability of specific co-applications for pre- or post-emergent uses and selectively will of course depend on the partners chosen.

The activity of dimethenarmid is described in the above mentioned patents and that of suitable herbicidal partners is described in the literature or on commercially available forms thereof (cf also CROP PROTECTION CHEMICALS REFERENCE, 9th edition (1993) Chemical & Pharmaceutical Press, NY, N.Y.; The Pesticide Manual, 9th edition (1991), British Crop Protection Council, London; Ag Chem New Product Review, Ag Chem Information Services, Indianapolis, Indiana; Farm Chemicals Handbook, 1993 edition, Meister Publishing Company, Willoughby, Ohio and the like).

The invention also provides herbicidal or plant growth regulating compositions comprising an herbicidally effective aggregate amount of dimethenamid and at least one other herbicide.

Such compositions contain the active substances in association with agriculturally acceptable diluents. They may be employed in either solid or liquid forms e.g. in the form of a wettable powder or an emulsifiable concentrate, incorporating conventional diluents. Such compositions may be produced in conventional manner, e.g. by mixing the active ingredient with a diluent and optionally other formulating ingredients such as surfactants and oils.

The term diluents as used herein means any liquid or solid agriculturally acceptable material which may be added to the active constituent to provide a more easily or improved applicable form, or to achieve a usable or desirable strength of activity. Examples of diluents are talc, kaolin, diatomaceous earth, xylene, non-phytotoxic oils, or water.

Particular formulations, to be applied in spraying forms such as water dispersible concentrates or wettable powders, may contain surfactants such as wetting and dispersing agents. e.g. the condensation product of formaldehyde with naphthalene sulphonate, an alk,larylsulphonate, a lignin sulphonate, a fatty alkyl sulphate. an ethoxylated alkylphenol or an ethoxylated fatty alcohol.

In general, the formulations include from 0.01 to 90% by weight of active agent(s) and from 0 to 20% by weight of agriculturally acceptable surfactant, the active agent consisting of dimethenamid and at least one other herbicide. Concentrate forms of compositions generally contain between about 2 and 90%, preferably between about 5 and 80% by weight of active agent. Application forms of formulation may for example contain from 0.01) to 20% by weight of active agent.

When employing concurrent, immediately sequential or tank mix applications the herbicide partner(s) can be employed in commercially available form if appropriate and at rates equivalent to or preferably below those recommended by the manufacturer or in the references cited above. Dimethenamid can also be applied in commercially available form (e.g. as FRONTIER® herbicide) or as formulated e.g. as described in the above-mentioned U.S. Pat. No. 4,666,502.

On co-application according to the present invention other compounds having biological activity, e.g. compounds having insecticidal or fungicidal activity, may also be included.

The preferred mode of application is tank mix prepared e.g. by adding dimethenamid to a tank containing the other herbicide partner and an appropriate surfactant or vice versa depending on the type of herbicide partner chosen. It is advisable to consult labels of mixing partners and to conduct compatibility tests prior to mixing.

Depending on the choice of co-application partners both pre- and post-emergence activity on a large range of broadleaf and grassy weeds may be achieved. Examples of such weeds are Agropyron repens—quackgrass
Brachiaria platyhylla—broadleaf signalgrass
Bromus spp—e.g. downybrome
Cenchrus spp.—e.g. southern sandbur, sandbur, field sandbur
Dactyloctenium aegyptium—crowfootgrass
Dizitaria spp—e.g. crabgrass, smooth crabgrass, large crabgrass
Echinochloa crus-galli—barnyardgrass
Eleusine indica—goosegrass
Eriochloa spp.—e.g. southwestern cupgrass, prairie cupgrass, woolly cupgrass
Leptochloa filiformis—red spangletop
Oryza sativa—red rice
Panicum spp—e.g. witchgrass and fall-, browntop- and texas-panicum, wild proso millet
Poa annua—annual bluegrass
Setaria spp—e.g. giant foxtail, foxtail miillet, yellow foxtail, bristly foxtail, green foxtail
Sorghum almum—sorghum almum Sorghum bicolor—shattercane
Sorghum halepense—seedling johnson grass
Urochloa panicoides—liverseedgrass
Acanthospermum hispidum—bristly starbur
Amaranthus spp—e.g. pigweed, tumble pigweed; smooth pigweed. redroot pigveed, prostrate pigweed, waterhemp, spiny amaranth
Ambrosia artemisiifolia—common ragweed
Bidens pilosa—hairy beggarticks
Capsella bursa-pastoris—shepherdspurse
Chenopodium album—common lambsquarters
Cleome monophylla—spindlepod
Commelina spp—e.g. dayflower
Crotalaria sphaerocarpa—
Datura stranionium—jimsonweed
Desmodium tortuosum—Florida beggarweed
Euphorbia nutans—nodding spurge
Euphorbia maculata—spotted spurge
Galinsoga parviflora—smallflower galinsoga
Ipomea spp—e.g. ivyleaf-, tall-, pitted morningglor
Lamium purpureum—purple deadnettle
Matricaria chamomilla—wild chamomile
Mollugo verticillata—carpetweed
Papaver rhoeas—corn poppy
Polygonum spp—e.g. smartweed, annual smatweed, wild buckwheat. prostrate knotweed
Portulaca oleracea—common purslane
Richardia scabra—Florida pusley
Schkuhria pinnata—dwarf marigold
Sida spinosa—prickly sida
Solanum spp.—e.g. black nightshade, E. black nightshade, hairy nightshade, silverleaf nightshade
Stellaria media—common chickweed
Tazetes minuta—wild marigold (khaki weed)
Cyperus esculentis—yellow nutsedge
Cyperus iria—rice flatsedge In addition the following weeds may also be controlled when employing appropriate mixing partners.
Abutilon theophrasti—velvetleaf
Hibiscus trionum—Venice mallow
Avena fatua—wild oats
Sinapis alba—white mustard
Xanthium strumarium—common cocklebur
Cassia obtusifolia—sicklepod
Apera spica-venti—windgrass
Campsis radicans—trumpet creeper
Rottboellia exaltata—itchgrass
Cynodon dactylon—bermudagrass
Lespedeza spp.—e.g. lespedezas
Trifolium spp.—e.g. clovers
Hippuris vulyaris—marestail
Asclepias spp.—e.g. milkweeds
Salvia—e.g. lanceleaf sage
Salsola iberica—Russian thistle
Convolvulus arvensis—field bindweed
Cirsium arvense—Canada thistle
Proboscidea louisianica—devilsclaw
Senecio spp.—e.g. common groundsel
Chorispora tennela—blue mustard
Alopecurus myosuroides—blackgrass
Sisymbrium altissimum—tumble mustard
Caperionia palustris—texasweed Crop selectivity will also usually depend upon choice of partners. Dimethenamid exhibits excellent selectivity in corn (maize), soybean and several other crops.

Examples of particular partners for co-application with dimethenamid include these selected from one or more of the types listed under a) through w) below.

a. benzoic acids, e.g. dicamba
b. picolinic acids and related compounds, e.g. picloram, triclopyr, fluroxypur, clopyralid
c. phenoxys, e.g. 2,4-D, 2,4-DB, triclopyr, MCPA. MCPP, 2,4: -DP, MCPB
d. other chloracetamides, e.g. alachlor, acetochlor, metolachlor, diethatyl, propachlor, butachlor, pretilachlor, metazachlor, dimethachlor especially metolachlor, alachlor, acetochlor
e. amides, e.g. propanil, naptalam
f. carbamates, e.g. asulam
g. thiocarbamates, e.g. EPTC, butylate, cvcloate, molinate, pebulate, thiobencarb, triallate, vernolate
h. nitriles, e.g. bromoxynil, ioxynil
i. ureas, e.g. diuron, thidiazuron. fluometuron, linuron, tebuthiuron, forchlorfenuron
j. triazines, e.g. atrazine, metribuzin, cyanazine, simazine, prometon, ametryn, prometryn, hexazinone
k. diphenyl ethers, e.g. acifluorfen, fomesafen, lactofen, oxyfluorfen
l. dinitroanilines, e.g. trifluralin, prodiamine, benefin, ethalfluralin, isopropalin, oxyzalin, pendimethalin
m. sulfonylureas e.g. rimsulfuron, metsulfuron, nicosulfuron, triasulfuron, prirnisulfuron, bensulfuron, chlorimuron, chlorsulfuron, sulfometuron, thifensulfuron, tribenuron, ethametsulfuron, triflusulfuron, clopyrasulfuron, pyrazasullfuron, pro-sulfuron (CGA-152005), halosulfuron, netsu Iro n-methyl, chlorimuron-ethyl;
n. irnidazolinones, e.g. imazaquin, imazamethabenz, imazapyr, imazethapyr, imazmethapyr
o. cyclohexanediones, e.g. sethoxydim
p. aryloxyphenoxys, e.g. fluazifop
q. bipyridiliums, e.g. paraquat, diquat
r. pyridazinones, e.g. norflurazon
s. uracils, e.g. bromacil, terbacil
t. isoxazolones, e.g. clomazone
u. various, e.g. glyphosate, glufosinate, methazole, paclobutrazol, bentazon, desmedipham, phenmedipham, pyrazon, pyridate, arnitrole, fluridone, DCPA, dithiopyr, pronarnide, bensulide, napropamnide, siduron, flumetsulam, sethoxydim, fluazifop, clethodim, diclofop-methyl, fenoxaprop-ethyl, haloxyfop- methyl, quizalofop, diclobenil, isoxabenz, oxadiazon, paclobutrazol, ethofumesate, quinclorac, difenzoquat, entothall, fosainine, DSMA, MSMA
v. Group 11a "others" as described above.
w. Group 11b "others" as described above.

Especially preferred partners among groups a) through w) are those of groups a), m), n), u) and v), i.e. the sulfonylureas and the triketones and diones.

The co-application of the combination of dimethenamid and triketone(s) or dione(s) according to present invention is especially suitable in crops of monocotyledons, such as cereals, maize and rice. However, application in maize corps being infested with monocotyledonous and dicotyledonous weeds is most advantageous, as harmful effects against the crop plants are not enhanced. Both pre- and postemergence application to the undesired weeds is possible with this preferred combination. However, the preferred time point of application in maize is after emergence of the maize seedlings.

Application rates for co-application of dimethenamid and a triketone or dione will of course vary depending upon climatic conditions, season, soil ecology, weeds to be combatted and the like, however, successful results can be obtained, e.g. in co-application with rates of the triketone or dione which are significantly lower than recommended for use thereof alone; e.g. 0.01 to 2 kg/ha, preferably 0.1 to 1 kg/ha. especially 0.1 to 0.6 kg/ha.

From this group, combinations are preferred wherein the triketone or dione is selected from 4-(4-chloro-2-nitrobenzoyl)-2,6,6-trimethyl-2H-1,2-oxazine-3,5-(4H,6H) dione, and sulcotrione, with sulcotrione being preferred.

The most preferred combination of this type is that of sulcotrione and dimethenamid. The mixture ratio will be determined according to the specific soil, crop and climate condition of use. As an example the co-application rates will be in the range of 0.9 to 1.5 kg/ha of dimethenamid and 0.15 to 0.45 kg/ha of sulcotrione. The ratio of the active ingredient in the composition by weight of sulcotrione and dimethenamid is between 1:2 and 1:10.

For the co-application in a preferred 3-way mix comprising dimethenamid and a triketone or dione of group v), the third component is preferably selected from the group j), i.e. the group of triazine herbicides. In a typical 3-way mix the triazine component will be present in a ratio of 3:1 to 1:3 relative to the dimethenamid content, with an excess of dimethenamid being preferred, i.e. a preferred ratio of 1:1 to 1:3, e.g. 1:1.5. The preferred triazine herbicide in this type of a 3-way mix is atrazine.

The co-application of the combination of dimethenamid and sulfonylurea(s) according to present invention is especially suitable in crops of monocotyledons, such as cereals, maize, sucar cane and rice. For example, application in sugar cane being infested with monocotyledonous and dicotyledonous weeds is particularly advantageous, as the harmful effects against the crop plants are not enhanced, but the weeds are controlled very effectively. Both pre- and postemergence applications to the undesired weeds is possible with this combination. However, the preferred time point of application to sugar cane is after emergence of the sugar cane seedlings, or transplantation of ratoon cane.

In this use the application rates for co-application of dimethenamid and a sulfonylurea will of course vary depending upon climatic conditions, season, soil ecology, weeds to be combatted and the like, however, successfull results can be obtained, e.g. in co-application with rates of the sulfonylurea which are significantly lower than the recommended use thereof alone; e.g. 1 to 150 g/ha, preferably 10 to 100 g/ha.

From this group the preferred combination for control of weeds in sugar cane is one wherein the sulfonylurea is chlorimuron. The mixture ratio will be determinable according to the specific soil, crop and climate condition of use. As an example the co-application rates will be in the range of 0.9 to 3.0 kg/ha of dimethenamid and 10 to 100 g/ha of chlorimuron. For the combatting of cyperus spp. in sugar cane crop they may be for example 2.0 to 3.0 kg/ha of dimethenamid and 50 to 90 g/ha of chlorimuron. The ratio of active ingredient in the composition by weight of chlorimuron and dimethenamid is between 1:3000 and 1:20, preferably 1:30 to 1:60, e.g. 1:34 or 1:38 or 1:45.

For the co-application in a preferred 3-way mix comprising dimethenamid and a sulfonylurea of group m), the third component is preferably selected from the group i), i.e. the group of urea herbicides. In a typical 3-way mix the urea component will be present in a ratio of 2:1 to 1:4, relative to the dimethenamnid content, with an excess of dimethenamid being preferred, i.e. a preferred ratio of 1:1 to 1:3, e.g. 1:2. The preferred urea herbicide in this type of a 3-way rnix is diuron.

It will be appreciated that mixtures of dimethenamid with more than one herbicide e.g. 3-way rrixes are also included within the purview of the invention.

Examples of specific mixing partners can be selected for example from the following: paraquat (e.g. as GRAMOXONE® or GRAMOXONE®EXTRA), simazine (e.g. as PRINCEP®), glyphosate (e.g. as ROUNDUP®), glufosinate (e.g. as BASTA®); (Compound Group I).

Further examples of specific mixing partners can be selected from the following: atrazine, cyanazine (e.g. as BLADEX® or together with atrazine as EXTRAZINE® or EXTRAZINE®II) terbutylazine, pendimethalin (e.g. as PROWL®), metribuzin, linuron (Compound Group II).

Further examples of specific mnixing partners can be selected from the following: nicosulfuron (e.g. as ACCENT®) rimsulfuron (e.g. as TITUS®) and primisulfuron (e.g. as BEACON®) (Compound Group III).

Further examples of specific mixing partners can be selected from the following imazethapyr (e.g. as PURSUIT®), imazaquin (e.g. as SCEPTER®), chloramben, aclonifen (Compound Group IV).

Further examples of specific mixing partners can be selected from the following: dicamba (e.g. as BANVEL®, as CLARITY® (in DGA salt form) or together with atrazine as MARKSMAN®).

Further examples of specific mixing partners can be selected from sethoxydim (e.g. as POAST®), fluazifop (e.g. as FUSILADE®) (Compound Group V).

Further examples of specific mixing partners can be selected from the following: sulcotrione (e.g. as MIKADO®) and 4-(4-chloro-2-nitro-benzoyl)-2,6,6-trimethyl-2H-1,2-oxazine-3,5-(4H,6H) dione (Compound Group VI).

Further examples of specific mixing partners for 3-way mix are sulcotrione (e.g. as MIKADO®) and atrazine (e.g. as GESAPRIM®) (Compound Group VI).

Further examples of specific mixing partners include chlorimuron (e.g. as CLASSIC® or in a 3-way mix together with diuron as FRONT®) (Compound Group VII).

According to the desired weed spectrum, time of application and the like other specific herbicides listed within the groups a) through w) above are also particular examples of suitable mixing partners.

It has now also been found that very efficient control of grassy weeds in crops of sugar cane can also be with herbicides of the class of chloracetamides in co-application with at least one herbicide of the class of sulfonylurea herbicides (group m) optionally in the presence of at least one herbicide of the class of the urea herbicide (group i). These components synergistically enhance the herbicidal effect of the mixture. The chloroacetamides are widely used in agricultural practice. Preferred species of this group are inter alia Alachlor (LASSO®) whose chemical designation is 2-chloro-2',6'-diethyl-N-methoxymethyl-acetanilide; Acetochlor (HARNESS®) whose chemical designation is 2-chloro-N-(ethoxymethyl)-N-(2-ethyl-6-methylphenyl) acetamide; Metolachlor (DUAL®) whose chemical designation is 2-chloro-6'-ethyl-N-(2-methoxy-1 -methylethyl)-aceto-toluidide; Metazachlor (BUTISAN S®) whose chemical designation is 2-chloro-N-(pyrazol-1-yl-methyl) acet-2',6'-xylidide; and dimethenamid (FRONTIER®) whose chemical designation is 2-chloro-N(2,4-dimethyl-3-thienyl)-N-(2-methoxy-1-methylethyl)-acetamide.

Application rates of chloroacetamides for co-application will of course vary depending upon climatic conditions, season, soil ecology, weeds to be combatted and the like, however, successful results in sugar cane can be obtained e.g. with rates of the chloroacetamide of 1 to 6 kg/ha, preferably 2 to 5.5 kg/ha in co-application with sulfonylurea and urea herbicides. For example the specific application rates of the chloroacetamide component is 3 to 6 kg/ha for Alachlor, e.g. 5.9 kg/ha, and 3 to 5 kg/ha for Metolachlor, e.g. 4.3 kg/ha.

The mixture ratio of the chloroacetamide herbicide with the sulfonylurea is generally between 20:1 and 300:1, preferably 20:1 to 100:1, e.g. 30:1 or 90:1. When a urea herbicide is co-applied with the mixture of a chloroacetamide and a sulfonylurea it may preferably be applied in a ratio of 1:1 to 1:5, relative to the chloroacetamide. e.g. I:'or 1:3 or 1:4. The preferred chloroacetamides other than dimethenamid to be applied in sugar cane with chlorimuron and diuron are acetochlor or metolachlor.

Thus, another aspect of present invention is the control of grassy weeds in sugar cane with a combination of a chloroacetamide in association with a sulfonylurea and an urea herbicide. Specific preferred combinations for this use are mixtures of dimethenamid, acetochlor, alachlor or metolachlor with a combination of chlorimuron and diuron, e.g in the commercially available 1:19 mixture FRONT®.

EXAMPLE 1

Active ingredients are weighed and dissolved in a stock solution consisting of acetone:deionized water, 1:1, and 0.5% adjuvant mixture consisting of surfactants SPAN® 20:TWEEN® 20:TWEEN® 85, 1:1:1. Dilutions from this stock solution are performed to allow for preparation of spray solutions consisting of single doses of individual or combined active ingredients. Each dose is applied simultaneously via a linear track sprayer set to deliver 600 liters/ha spray volume to both the foliage of the selected weed seedling species, postemergence application, and the surface of soil that had been previously sown with seeds, preemergence application. The seedlings used are cultured to develop plants at the two-to early three-leaf stage. The stage of development of each seedling at application time is recorded. After application, the treated plants are transferred to the greenhouse and held until termination of the experiment within four weeks. Symptoms of injurv are recorded two and ten days after postemergence application and fourteen days after preemergence application. Visual percentage ratings of crop injury and weed control are taken ten and twenty-eight days after postemergence application and fourteen and twentv-eight days after preemergence application.

Co-application of dimethenamid with other specific active ingredients such as outlined above produces improved herbicidal effects compared with application of each active ingredient alone.

EXAMPLE 2

A field trial is carried out employing dimethenamid (as FRONTIER® 7.5 EC) and nicosulfuron (as ACCENT® 75 WDG) in control of large crabgrass in corn. Application is as tankmix combination at early post-emergence of the weeds (3 and 4 leaf stages). Application rates of a.i. are 1.5 and 0.75 kg/ha for dimethenamid and 37.2 and 19.2 g/ha for nicosulfuron. Combined application of 0.75 kg/ha of dimethenamid and 19.2 g/ha of nicosulfuron gave 85% control with negligible corn damage compared with 35% for nicosulfuron applied alone at 19.2 g/ha and 72% for dimethenamid at a higher rate of 1.25 kg/ha. Combined application at the higher rate of dimethenamid with 37.2 g/ha of nicosulfuron gave an even more dramatic effect with 95% control compared with 72% for dimethenamid and only 45% for nicosulfuron each alone.

Similar effects are noticed on combined treatment of broadleaf weeds such as lambsquarters, prickly sida and morningglory employing 1.12 kg/ha of dimethenamid (as FRONTIER®) and 0.071 kg/ha of imazethapyr (as PURSUIT®).

EXAMPLE 3

Small field units in a maize field, infested with echinochloa crus galli and solanum nigrum are sprayed with a tank-mix suspension of dimethenamid and sulcotrione. The stage of the weeds is "full tillering" for echinochloa crus galli and "8-leaves stage" for solanum nigrum. The lot size is 8 meters in length and 3 meters in width. The application rates are 1.1 kg/ha of dimethenamid and 0.15 kg/ha of sulcotrione. Seven days after treatment the efficacy is evaluated, both as control of the weeds and as tolerance of the crop plants.

In this test the control of echinochloa was between 93 and 98% and the control of solanum was between 91 and 93% in three repetitions. while the damage of the maize plants was always below 10%.

EXAMPLE 4

Small field units in a maize field, infested with echinochloa crus galli, solanum nigrum and chenopodium album are sprayed with a tank-mix suspension of dimethenamid, sulcotrione and atrazine. The stage of the weeds is "full tillerinv" for echinochloa and "6–8 leaves stasge" for solanum and chenopodium. The lot size is 8 meters in length and 3 meters in broadth. The application rates are 1.08 kg/ha of dimethenamid. 150 or 210 g/ha of sulcotrione and 750 g/ha of atrazine. 14 days after treatment the efficacv is evaluated. The results (in percentage control) were as follows:

| Compound a.i./ha | | expected additive effect | synergistic effect |
|---|---|---|---|
| | Echinochloa control | | |
| Atrazine 1500 | 23 | — | |
| Dimethenamid/Atrazine 1080/750 | 30 | — | |
| Sulcotrione/Atrazine 150/750 | 26 | — | |
| Sulcotrione/Atrazine 210/750 | 33 | — | |
| Dimethenamid/Sulcotrione/ Atrazine 1080/150/750 | 95 | 56 | +39 |
| Dimethenamid/Sulcotrione/ Atrazine 1080/210/750 | 97 | 59 | +42 |
| | Solanum/ Chenopodium | | |
| Atrazine 1500 | 16 | – | |
| Dimethenamid/Atrazine 1080/750 | 36 | – | |
| Sulcotrione/Atrazine 150/750 | 23 | – | |
| Sulcotrione/Atrazine 210/750 | 53 | – | |
| Dimethenamid/Sulcotrione/ Atrazine 1080/150/750 | 97 | 53 | +44 |
| Dimethenamid/Sulcotrione/ Atrazine 1080/210/750 | 100 | 89 | +11 |

The synergistic effect is clearly visible at the lower rates of sulcotrione, resulting in a nearly doubled degree of control, compared to the expected additive efficacies. For the higher rates of sulcotrione, (>300 g/ha) only the additive effect remains visible since the total control is 100%.

EXAMPLE 5

A field trial is carried out on plots (2×20 m) planted with sugar cane and infested with cyperus rotundus in the first or second growing stags and sprayed with a backpack spraver in different concentrations in a tank mix. The amount of liquid spray broth is 400 l/ha. The application rates are 2.7 kg/ha of dimethenamid with 60 g/ha of chlorimuron or with 1.6 kg/ha of a fixed ratio mixture of chlorimuron and diuron (1:19) which is commercially available as FRONT®. Visual evaluation is done 30 or 60 davs after treatment (DAT) in percentage of control. The expected additive effect value is calculated according to the method of Colby:

| Compound a.i./ha conditions | Cyperus Control (DAT) | expected additive effect | synergistic effect |
|---|---|---|---|
| light to medium soil | | | |
| Dimethenamid 2.7 kg | 19 (60 DAT) | — | |
| Chlorimuron/Diuron 1.6 kg | 45 (60 DAT) | — | |
| Dimethenamid/ Chlorimuron/Diuron 2.7 + 1.6 kg | 76 (60 DAT) | 55 | +21 |
| heavy soil | | | |
| Dimethenamid 2.7 kg | 10 (60 DAT) | — | |
| Chlorimuron/Diuron 1.6 kg | 37 (60 DAT) | — | |
| Dimethenamid/ Chlorimuron/Diuron 2.7 + 1.6 kg | 74 (60 DAT) | 43 | +31 |
| light to medium soil | | | |
| Dimethenamid 2.25 kg | 23 (30 DAT) | — | |
| Chlorimuron/Diuron 1.2 kg | 48 (30 DAT) | — | |
| Dimethenamid/ Chlorimuron/Diuron 2.25 + 1.2 kg | 80 (30 DAT) | 60 | +20 |
| light to medium soil | | | |
| Dimethenamid 2.7 kg | 27 (30 DAT) | — | |
| Chlorimuron/Diuron 1.2 kg | 48 (30 DAT) | — | |
| Dimethenamid/ Chlorimuron/Diuron 2.7 + 1.2 kg | 88 (30 DAT) | 62 | +26 |
| light to medium soil | | | |
| Dimethenamid 2.7 kg | 27 (30 DAT) | — | |
| Chlorimuron 0.06 kg | 58 (30 DAT) | — | |
| Dimethenamid/ Chlorimuron 2.7 + 0.06 kg | 93 (30 DAT) | 69 | +24 |

The achieved results indicate that synergistic effects are obtained with the 2-way mix (dimethenamid/chlorimuron), as well as with the 3-way mix (dimethenamid/ chlorimuron/ diuron).

EXAMPLE 6

In the procedure as set out in Example 5, tank mixtures of 5.7 kg/ha of alachlor or 4.3 kg/ha of metolachlor with 1.2 kg/ha of the fixed ratio mixture of chlorimuron and diuron (1:19; comnmercial FRONT®) where applied to a sugar cane field. The results were as follows:

| Compound a.i./ha conditions | Cyperus Control (DAT) | expected additive effect | synergistic effect |
|---|---|---|---|
| light to medium soil | | | |
| Alachlor 5.4 kg | 30 (30 DAT) | — | |
| Chlorimuron/Diuron 1.2 kg | 48 (30 DAT) | — | |
| Alachlor/Chlorimuron/ Diuron 5.4 + 1.2 kg | 85 (30 DAT) | 64 | +21 |
| light to medium soil | | | |
| Metolachlor 4.3 kg | 23 (30 DAT) | — | |
| Chlorimuron/Diuron 1.2 kg | 48 (30 DAT) | — | |
| Metolachlor/Chlorimuron/ Diuron 4.3 +1.2 kg | 89 (30 DAT) | 60 | +29 |

What is claimed is:

1. A herbicidal composition comprising a herbicidally effective amount of dimethenamid, a substituted urea herbicide, and an agriculturally acceptable carrier.

2. The composition ot claim 1 wherein said substituted urea herbicide is selected from the group consisting of diuron, fluometuron, linuron, tebuthiuron, thidiazuron, and forchlorfenuron.

3. The composition of claim 1 wherein said substituted urea herbicide is diuron.

4. The composition of claim 1 wherein the amount of dimethenamid is such that it can be applied at a rate from 0.1 to 3.0 kg/ha.

5. The composition of claim 1 wherein the amount of dimethenamid is such that it can be applied at a rate from 0.25 to 1.5 kg/ha.

6. The composition of claim 1 wherein the amount of substituted urea herbicide is such that it can be applied at a rate from 0.1 to 3.0 kg/ha.

7. A method of controlling undesired plant growth in the presence of crop compilsing applyinlg to the locus of said undesired plant growth a herbicidally effective aggregate amount of dimethenamid and a substituted urea herbicide wherein the application rate of dimetheniumid is from 0.1 to 3.0 kg/ha.

8. The method of claim 7 wherein the application rate of the substituted urea herbicide is from 0.1 to 3.0 kg/ha.

9. The method of claim 7, wherein the application rate of dimethenamid is from to 0.25 to 1.5 kg/ha.

10. The method of claim 7 wherein the substituted urea harbicide is is selected from the group consisting of diuron, fluometuron, linuron, tebuthiuron, thidiazuron, and forchlortenuron.

11. The method of claim 7 wherein the substituted urea herbicide is diuron.

12. The method of claim 7 wherein the crop is corn or soybean.

13. The method or claim 7 wherein the undesired plant growth to be controlled is a grassy weed.

14. The method of claim 7 wherein the undesired plant growth is a broad leaf.

15. The method of claim 7 wherein said applying step comprising co-applying dimethenamid and a tsubstituted urea herbicide in a tank mix.

16. The method of claim 7 wherein said applying step comprises the preemergent coapplication of dimethenamid and a substituted urea herbicide.

17. The method of claim 7 wherein said applying step comprises the postemergent coapplication of dimethenamid and a substituted urea herbicide.

18. The method of claim 7 wherein said applying step comprises applying the herbicides simultaneously to the locus of said undesired plant growth.

19. The method of claim 7 wherein said applying step comprises applying the herbicides sequentially to the locus of said undesired plant growth.

20. A method of potentiating the herbicidal effect of a substituted urea herbicide comprising combining a substituted urea herbicide with a potentiating effective amount of dimethenamid to produce a herbicidally effective composition.

\* \* \* \* \*

UNITED STATES PATENT AND TRADEMARK OFFICE
CERTIFICATE OF CORRECTION

PATENT NO. : 5,900,389
DATED : May 4, 1999
INVENTOR(S) : Fenderson et al.

It is certified that error appears in the above-indentified patent and that said Letters Patent is hereby corrected as shown below:

Title page, item [54], line 3 and Column 1, line 3:
In the title, "HERBICIDIES" should read --HERBICIDES--.

Column 12, line 5, "ot" should read --of--; line 21, "crop compilsing applyinlg" should read --a crop comprising applying--; line 24, "dimetheniumid" should read --dimethenamid--; line 31, "harbicide" should read --herbicide--; lines 32-33, "forchlortenuron" should read --forchlorfenuron--; line 41, "broad leaf" should read --broadleaf weed--; line 43, "tsubstituted" should read --substituted--.

Signed and Sealed this

Twenty-sixth Day of October, 1999

Attest:

Q. TODD DICKINSON

*Attesting Officer*  *Acting Commissioner of Patents and Trademarks*